(12) United States Patent
Willson et al.

(10) Patent No.: US 9,156,863 B2
(45) Date of Patent: Oct. 13, 2015

(54) BRANCHED SILOXANES AND METHODS FOR SYNTHESIS

(75) Inventors: C. Grant Willson, Austin, TX (US); Tsuyoshi Ogawa, Austin, TX (US); B. Michael Jacobsson, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 4 days.

(21) Appl. No.: 13/577,004

(22) PCT Filed: Feb. 16, 2011

(86) PCT No.: PCT/US2011/025065
§ 371 (c)(1),
(2), (4) Date: May 21, 2013

(87) PCT Pub. No.: WO2011/103176
PCT Pub. Date: Aug. 25, 2011

(65) Prior Publication Data
US 2013/0281713 A1    Oct. 24, 2013

Related U.S. Application Data

(60) Provisional application No. 61/306,227, filed on Feb. 19, 2010.

(51) Int. Cl.
*C07F 7/08* (2006.01)
*C07D 303/12* (2006.01)
*C07D 301/00* (2006.01)

(52) U.S. Cl.
CPC ............ *C07F 7/0874* (2013.01); *C07D 301/00* (2013.01); *C07D 303/12* (2013.01); *C07F 7/0849* (2013.01); *C07F 7/0879* (2013.01); *C07F 7/0889* (2013.01)

(58) Field of Classification Search
CPC .... C07F 7/0874; C07F 7/0879; C07F 7/0889; C07F 7/0849; C07D 301/00; C07D 303/12
USPC .................... 549/215; 556/437, 451
See application file for complete search history.

(56) References Cited

U.S. PATENT DOCUMENTS

| | | | |
|---|---|---|---|
| 4,633,003 A | 12/1986 | Falcetta et al. ............... | 556/419 |
| 5,256,741 A | 10/1993 | Ogawa et al. ............... | 525/477 |
| 6,828,404 B2 * | 12/2004 | Crivello ............... | 528/25 |
| 7,244,799 B2 | 7/2007 | Prasad et al. ............... | 528/14 |
| 2003/0232900 A1 | 12/2003 | Irifune ............... | 522/6 |

FOREIGN PATENT DOCUMENTS

WO    WO 2011/049078    4/2011

OTHER PUBLICATIONS

Lin, M. W., Simulation and design of planarizing materials for reverse-tone step and flash imprint lithography, J. Micro.Nanolith. MEMS MOEMS 7(2), 023008 (Apr.-Jun. 2008).*
Lin, Michael W.,"Simulation and design of planarizing materials for reverse-tone step and flash imprint lithography." Journal of Micro/Nanolithography, MEMS, and MOEMS 7.2 (2008): 023008-023008.*
Lassen, C., et al. "Siloxanes-consumption, toxicity and alternatives." Environmental Project 1031 (2005), p. 1-111.*
Crivello, J. V., "The discovery and development of onium salt cationic photoinitiators." Journal of Polymer Science Part A: Polymer Chemistry 37.23 (1999): 4241-4254.*
Morgan, A.R. "Diels-alder adducts of vinyl porphyrins: synthesis and in vivo photodynamic effect against a rat bladder tumor." Journal of medicinal chemistry 33.4 (1990): 1258-1262.*
U.S. Appl. No. 11/571,071, filed Jun. 17, 2005, Ryuzaki, et al.
Hao, et al., "Photocurable Silicon-Based Materials for Imprinting Lithography." 651729 (2007).
Jen, et al., "Multilevel Step and Flash Imprint Lithography for Direct Patterning of Dielectrics." 65170K (2007).
Yoshino, et al., "A Convenient Synthesis of A,Ω-Difunctionalized Linear Dimethylsiloxanes with Definite Chain Lengths." *Chemistry Letters*, 19(11):2133-2136 (1990).
Zhang and Laine. "Hydrosilylation of Allyl Alcohol with [HSiMe$_2$OSiO$_{1.5}$]$_8$: Octa (3-Hydroxypropyldimethylsiloxy)octasilsesquioxane and Its Octamethacrylate Derivative as Potential Precursors to Hybrid Nanocomposites." *J. Am. Chem. Soc.*, 122:6979-6988 (2000).
ISR PCT/US2011/025065; and.
Gustavson, et al., "Metal Complex-Catalyzed Redistribution Reactions of Organosilanes: IV. Redistribution Reactions of Methylsiloxanes Catalyzed by Transition Metal Complexes." *J. Organometallic Chemistry*, 238(1):87-97 (1982).

* cited by examiner

*Primary Examiner* — Noble Jarrell
*Assistant Examiner* — John Mauro
(74) *Attorney, Agent, or Firm* — Medlen & Carroll, LLP

(57) ABSTRACT

The present invention describes branched and functionalized siloxanes and methods for making such compounds. The compounds have a variety of uses. One preferred application is as novel planarizing material for lithography, in which case functionalized branched siloxane, such as an epoxy-modified branched siloxane is particularly useful.

3 Claims, 18 Drawing Sheets epoxy-Si-12

Functionalized Si-12

FIGURE 11

| Name | Epoxy-Si-12 |
|---|---|
| Structure | (chemical structure) |
| Appearance | Slightly yellow liquid |
| Molecular weight | 1124.22 |
| Si containing | 30.0 % |
| Vapor pressure (25 C) | 0.65 Torr |
| Viscosity (25 C) | 29 cP |
| Density | 0.96 g/ml |
| Surface tension | 20.7 dyne/cm |
| UV shrinkage | 2.2 % |

Resist drop layout

Total resist drop amount: 0.0195 ul
Template down velocity: 0.45 mm/s
Template cavity pressure: 0.05 bar
Imprint force: 15 N
Pre UV delay: 120 sec.
UV exposure: 20 sec.

BRANCHED SILOXANES AND METHODS FOR SYNTHESIS

FIELD OF THE INVENTION

The present invention relates to branched siloxanes and methods for synthesis of branched siloxanes, including, but not limited to, functionalized branched siloxanes. Such compounds have many uses including multiple applications in the semiconductor industry including planarizing layers, patternable insulators, and the like.

BACKGROUND OF THE INVENTION

Liquid branched siloxanes having low viscosity, low vapor pressure and high silicon content are useful for the semiconductor industry such as the manufacturing of micro processors, flash memory, visual display devices and optical devices (light emitting diodes), etc. For example, Michael Lin et al. reported a UV curable liquid branched siloxane named Si-14 for the use in nano imprint lithography [1, 2]. They concluded that Si-14 functionalized with methacrylate as UV cross-linkable groups showed promising properties as planarizing layer on topology, patternable material and etch barrier. This is because of its properties (low viscosity 15 cP, low vapor pressure 0.8 Torr at 25° C., low UV shrinkage 5.0%, and with a high silicon content of 33%). However the synthetic route for Si-14 requires many steps as shown in FIG. 2. The reaction gave low yield (<20%) and took several days (>12 days) to synthesize, therefore the route was not amendable to scaling to become a commercial product.

What is needed is a simpler synthesis that provides high yields in a short amount of time, and results in useful compounds.

SUMMARY OF THE INVENTION

The present invention contemplates branched siloxanes (both functionalized and unfunctionalized) as well as methods for making such compounds. In one embodiment, a method of synthesis is contemplated comprising reacting a siloxane which has silicon-hydrogen bond represented by the formula shown as (a) (where n represents a whole number between 1~20) with an asymmetric linear siloxane represented by the formula shown as (b) (where X represents any halogen and where m represents a whole number between 1 and 10, more preferably 2 and 10, and more commonly between 2 and 3) so as to generate a branched siloxane represented by the formula (c). This can be synthesized in a one step reaction shown in FIG. 1, using asymmetric linear siloxanes as reactants. The route provides a shortened synthetic path, high yields and reduces the feed stock cost by 70% compared to the stepwise route. The synthesis is significantly lower in cost and easily scalable. The branched siloxane (c) can be further treated to attach additional chemical moieties or functional groups as shown in FIG. 3.

In another embodiment, a method of synthesis is contemplated comprising reacting a siloxane represented by the formula shown as (e) (where x and y independently represent a whole number between 1~10) with an asymmetric linear siloxane represented by the formula shown as (b) (where X represents any halogen and where m represents a whole number between 1 and 10, and more commonly between 2 and 3) so as to generate a branched siloxane represented by the formula (f) (see FIG. 4). The branched siloxane (f) can be further treated to attach chemical moieties or functional groups such as that shown in FIG. 3 where X represents any but not limited to moieties selected from the group consisting of acrylates, methacrylates, vinyls, and epoxides.

The present invention contemplates, in one embodiment, a method for synthesizing branched siloxanes, comprising, reacting i) a siloxane which has a silicon-hydrogen bond represented by the formula (a), wherein n represents a whole number between 1 and 20, with ii) an asymmetric linear siloxane of formula (b), wherein X represents any halogen and m represents a whole number between 2 or 3, said reacting performed under conditions such that a branched siloxane and byproducts are produced. It is not intended that the present invention be limited by the nature of the siloxane used as a reactant. In one embodiment, said asymmetric linear siloxane is made from a cyclic compound. In one embodiment, said cyclic compound is hexamethylcyclotrisiloxane. In one embodiment, said siloxane comprising a silicon-hydrogen bond represented by the formula (a) is 3H, 5H-octamethyltetrasiloxane. In one embodiment, said 3H,5H-octamethyltetrasiloxane, prior to reacting with said asymmetric linear siloxane, is exposed to a catalyst in the presence of water. In one embodiment, said catalyst is removed prior to reacting said 3H, 5H-octamethyltetrasiloxane with said asymmetric linear siloxane. It is not intended that the present invention be limited to a particular catalyst, however, a palladium catalyst is a preferred catalyst. It is not intended that the present invention be limited to a particular halogen. However, the preferred halogen of said asymmetric linear siloxane is chlorine. In one embodiment, the present invention contemplates purifying the branched siloxane product free (or substantially free) of reactants and byproducts. In one embodiment, the present invention contemplates the further step of purifying the branched siloxane by distillation, so as to remove said byproducts (or at least the majority of byproducts, and preferably at least 90% of said byproducts) of the synthesis reaction and provide a purified branched siloxane. In one embodiment, the present invention contemplates the further step of functionalizing said purified branched siloxane. In one embodiment, said functionalizing comprises attaching chemical moieties; in a preferred embodiment, the chemical moieties are photo-crosslinkable moieties, said moieties selected from the group consisting of acrylates, methacrylates, vinyls and epoxides. In one embodiment, said functionalizing comprises hydrosilylation. The present invention also contemplates the compounds, as compositions of matter, described here, including but not limited to compounds made according to the above-described methods. For example, the present invention contemplates Si-12 having the structure shown in FIG. 10, as well as functionalized Si-12 (FIG. 6), such as epoxy-Si-12 (FIG. 5).

The compounds have a variety of uses. One preferred application is as a novel planarizing material for lithography, in which case functionalized branched siloxane, such as an epoxy-modified branched siloxane (epoxy-Si-12) is particularly useful. In one embodiment, the present invention contemplates spin coating formulations comprising functionalized branched siloxanes onto patterned substrates. In one embodiment, the present invention contemplates a planarizing layer comprising functionalized branched siloxanes made according to the methods of the present invention.

BRIEF DESCRIPTION OF THE DRAWINGS

For a more complete understanding of the features and advantages of the present invention, reference is now made to the detailed description of the invention along with the accompanying figures.

FIG. 11 is a table of properties of epoxy-Si-12.

DEFINITIONS

Figure 1:
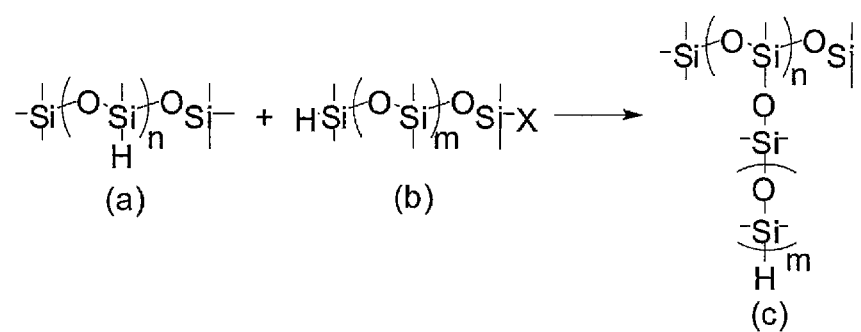
FIG. 1 shows a reaction for the synthesis of branched siloxanes in a one step reaction.
Figure 2:
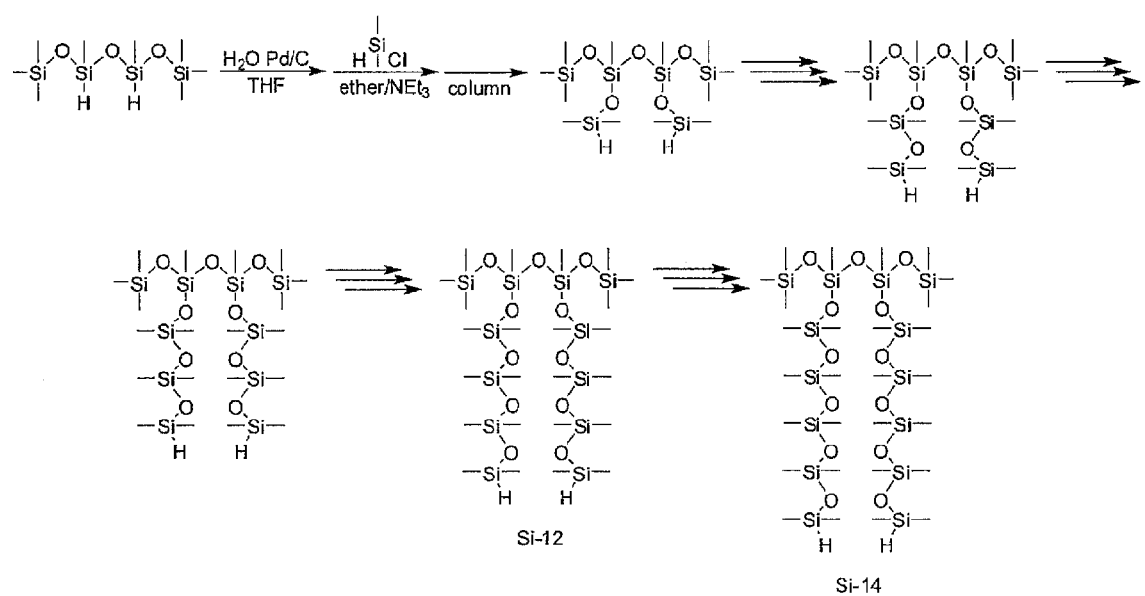
FIG. 2 shows a synthetic scheme for the synthesis of a branched siloxane material, Si-14, as previously reported in literature. This synthetic route is stepwise and requires several iterations to extend the branched siloxane chain resulting in low yields and a time intensive process.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

A siloxane is any chemical compound composed of units of the form $R_2SiO$, where R represents an atom or a group of atoms including but not limited to, a hydrogen atom, halogens, alkyl or aromatic groups. Siloxanes can have branched or unbranched backbones consisting of alternating silicon and oxygen atoms —Si—O—Si—O—, with side chains R attached to the silicon atoms. These siloxanes can be "functionalized" by adding particular chemical moieties having desirable functional properties (as described herein).

As used herein, "hydrogen" means —H; "hydroxy" means —OH; "oxo" means =O; "halo" means independently —F, —Cl, —Br or —I; "amino" means —$NH_2$ (see below for definitions of groups containing the term amino, e.g., alkylamino); "hydroxyamino" means —NHOH; "nitro" means —$NO_2$; imino means =NH (see below for definitions of groups containing the term imino, e.g., alkylamino); "cyano" means —CN; "azido" means —$N_3$; "mercapto" means —SH; "thio" means =S; "sulfonamido" means —$NHS(O)_2$— (see below for definitions of groups containing the term sulfonamido, e.g., alkylsulfonamido); "sulfonyl" means —$S(O)_2$— (see below for definitions of groups containing the term sulfonyl, e.g., alkylsulfonyl); and "silyl" means —$SiH_3$ (see below for definitions of group(s) containing the term silyl, e.g., alkylsilyl).

The term "alkylsilyl" when used without the "substituted" modifier refers to a monovalent group, defined as —$SiH_2R$, —SiHRR', or —SiRR'R", in which R, R' and R" can be the same or different alkyl groups, or any combination of two of R, R' and R" can be taken together to represent a dialkyl substituent. The groups, —$SiH_2CH_3$, —$SiH(CH_3)_2$, —$Si(CH_3)_3$ and —$Si(CH_3)_2C(CH_3)_3$, are non-limiting examples of unsubstituted alkylsilyl groups. The term "substituted alkylsilyl" refers —$SiH_2R$, —SiHRR', or —SiRR'R", in which at least one of R, R' and R" is a substituted alkyl or two of R, R' and R" can be taken together to represent a substituted dialkyl. When more than one of R, R' and R" is a substituted alkyl, they can be the same of different. Any of R, R' and R" that are not either substituted alkyl or substituted alkanediyl, can be either alkyl, either the same or different, or can be taken together to represent a dialkyl with two or more saturated carbon atoms, at least two of which are attached to the silicon atom.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include deuterium and tritium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Hexamethylcyclotrisiloxane is represented by the following structure:

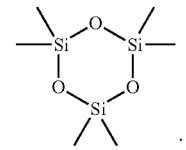

3H,5H-octamethyltetrasiloxane is represented by the following structure:

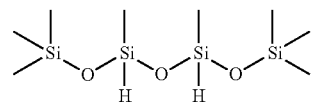

Dimethylchlorosilane is represented by the following structure:

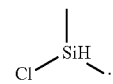

3-vinyl-7-oxabicyclo[4.1.0]heptane is represented by the following structure:

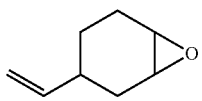

Bis(4-tert-butylphenyl)iodonium tris(trifluoromethylsulfonyl)methanide is represented by the following structure:

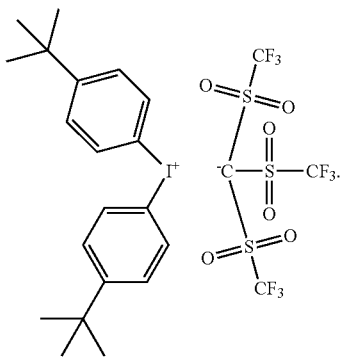

Photoacid generators (or PAGs) are typically cationic photoinitiators. A photoinitiator is a compound especially added to a formulation to convert absorbed light energy, UV or visible light, into chemical energy in the form of initiating species, viz., free radicals or cations. Cationic photoinitiators are used extensively in optical lithography. The ability of some types of cationic photoinitiators to serve as latent photochemical sources of very strong protonic or Lewis acids is the basis for their use in photoimaging applications. The usual photo-supplied catalyst has been strong acid. Triarylsulfonium and diaryliodonium salts have become the standard PAG ingredients in a chemically amplified resist formulations, because of their generally easy synthesis, thermal stability, high quantum yield for acid (and also radical) generation, and the strength and nonvolatility of the acids they supply. Simple onium salts are directly sensitive to DUV, X-ray and electron radiations, and can be structurally tailored, or mixed with photosensitizers, to also perform well at mid-UV and longer wavelengths. Nonionic PAGs such as phloroglucinyl and o,o-dinitrobenzyl sulfonates, benzylsulfones and some 1,1,1-trihalides are more compatible with hydrophobic media in general, although their thermal stabilities and quantum yields for acid generation are often lower.

It is not intended that the present invention be limited by the nature of the photoacid generator (PAG). There are several issues to be considered in the choice of the PAG, including but not limited to sufficient radiation sensitivity to ensure adequate strong acid generation for good resist sensitivity, absence of metallic elements, temperature stability, dissolution inhibition, etc. In one embodiment, triarylsulfonium (e.g. triphenylsulfonium nonaflate, or tri-p-hydroxyphenylsulfonium triflate) or diaryliodonium salts are preferred because of their generally easy synthesis, thermal stability, high quantum yield for strong acid (and also radical) generation, and the strength and nonvolatility of the acids they supply. It is also not intended that the present invention be limited by the developing solvents used. In one embodiment, the developing solvent can be an aqueous solution of an alkali metal hydroxide, such as sodium hydroxide or tetramethylammonium hydroxide.

DETAILED DESCRIPTION OF THE INVENTION

One embodiment of the synthetic route contemplated by the present invention is illustrated in FIG. 1. A desirable branched siloxane (c) is obtained by using siloxanes having silicon-hydrogen bond represented as (a) and asymmetric linear siloxanes represented as (b). The asymmetric linear siloxanes were prepared as described from a journal procedure in Yoshino et al. 1990 [3] starting with, for example, commercially available cyclic compounds. The reaction conditions were optimized such as determination of the amount of water and activated carbon needed. For example, one of the desirable linear siloxane (where m=2, X=Cl) was obtained as a colorless liquid in 77.9% yield at 99.7% purity (GC/MS).

The reaction using the siloxanes having silicon-hydrogen bond and asymmetric linear siloxanes give not only the desirable branched siloxanes, but also undesired byproducts. The most effective method of purification of the product is distillation. Column chromatography is ineffective to remove byproducts because they are also linear siloxanes that show similar properties (polarities) with the desirable branched siloxanes. After distillation, the desirable branched siloxanes are obtained as colorless liquid. Nuclear Magnetic Spectroscopy (NMR), $^1$H, $^{13}$C and $^{29}$Si, is useful to support the target structures. Matrix Assisted Laser Desorption Ionization (MALDI) spectroscopy (mass spectroscopy) also verify the desirable mass numbers.

Figure 9:
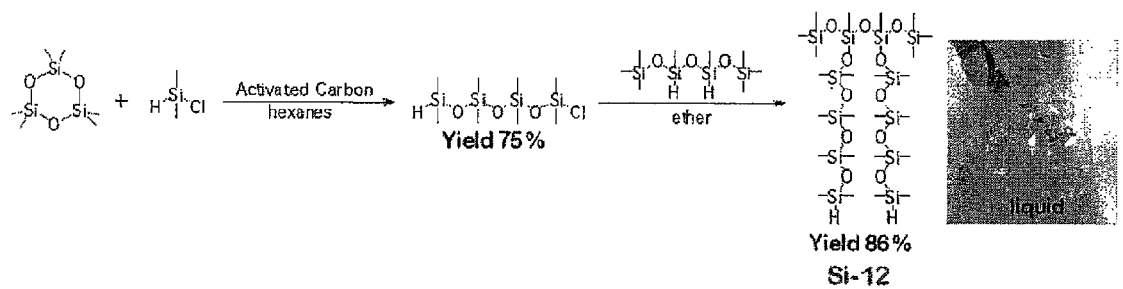
FIG. 9 shows the new synthetic route to obtain Si-12.

The new synthetic route to obtain Si-12 was successfully developed and is illustrated in FIG. 9. The optimized reaction to the final product, Si-12, took only two steps. This is a tremendous improvement in which the sought after product can be made in significantly higher yields and fewer steps compared to the previous synthetic route. The starting materials are relatively cheap and commercially available. The novel synthetic route has also been shown to be easily scalable and therefore suitable for industry.

Figure 10:
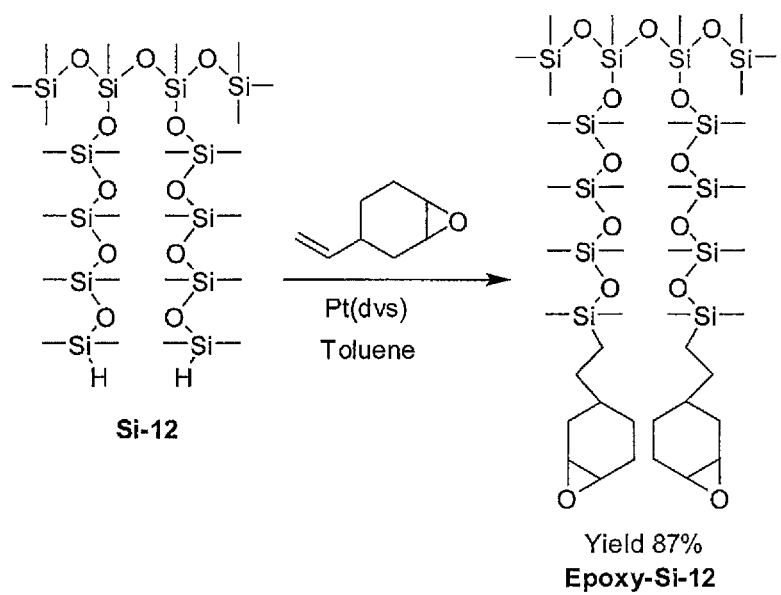
FIG. 10 shows the synthetic path to epoxy-Si-12.

Si-12 has two Si—H bonds, which can be converted to UV curable branched siloxanes. The synthetic path to epoxy-Si-12 is shown in FIG. 10. This type of reaction is referred to as a hydrosilylation. The reaction was successfully carried out and product was recovered in high yields (87%).

Figure 3:
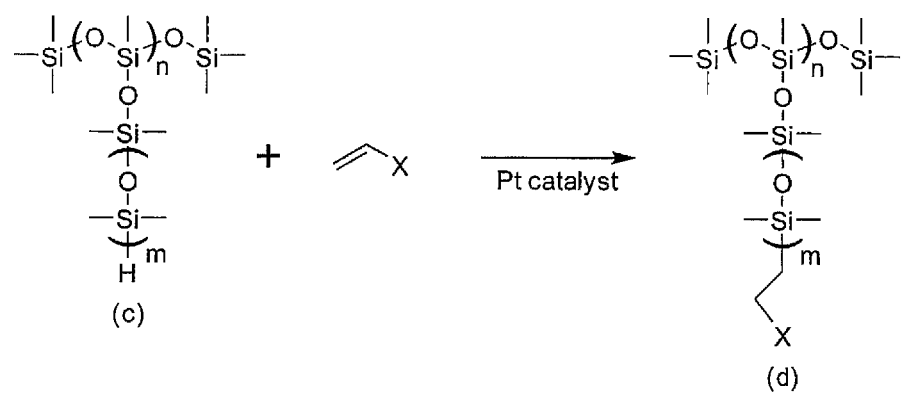
FIG. 3 shows a reaction of the current invention whereby branched siloxanes can be functionalized in a platinum catalyzed reaction. This process is referred to as a hydrosilylation.

The obtained branched siloxanes can be easily functionalized using authentic chemical reaction. For example, UV curable functional groups such as acrylates, methacrylates and epoxides can be introduced to the branched siloxanes via the Si—H moiety. The reaction is referred to as a hydrosilylation reaction and is illustrated in FIG. 3 where X is a chemical moiety having desired functional properties. Hydrosilylation, also called catalytic hydrosilation, describes the addition of Si—H bonds across unsaturated bonds. Ordinarily the reaction is conducted catalytically and usually the substrates are unsaturated organic compounds. Alkenes and alkynes give alkyl and vinyl silanes; aldehydes and ketones give silyl ethers. The functionalized branched siloxanes are tremendously useful in the semiconductor industry in processes including planarizing layers and patternable insulators.

Surface Hydrosilylation

The compounds described herein are useful for a variety of applications, including but not limited to, semiconductor fabrication. For example, a silicon wafer can be etched in hydrofluoric acid (HF) to remove the native oxide, and form a hydrogen-terminated silicon surface. Then the hydrogen-terminated surfaces can react with unsaturated compounds (such as terminal alkenes and alkynes), to form a stable monolayer on the surface. The hydrosilylation reaction can be initiated with UV light at room temperature, or with applied heat (typical reaction temperature 120-200° C.), under moisture and oxygen free conditions. The resulting monolayer is stable and inert, and prevents oxidation of the base silicon layer. Surfaces of this kind could find applications in areas such as molecular electronics, biochemistry, and direct electronic sensing of biomolecules.

Figure 4:
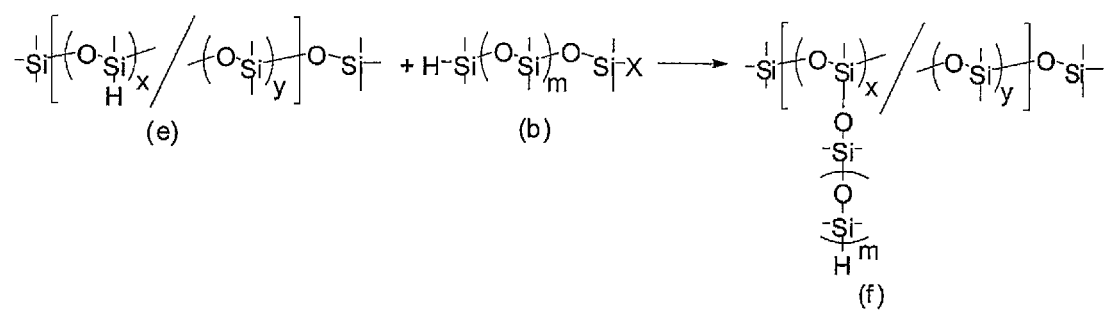
FIG. 4 shows a reaction in which the starting siloxane is varied.

In the present invention, it is possible to synthesize other branched siloxanes when starting siloxanes are changed to illustrated in (e), where x represents 1~10, y represents 1~10. The products are partially branched siloxanes shown in reaction shown in FIG. 4.

The compounds of the present invention can be used in layers as found in the Ryuzaki et al U.S. patent application Ser. No. 11/571,017 [5], herein incorporated by reference.

The branched siloxanes can be functionalized with photo crosslinkable groups such as acrylates, methacrylates, vinyls or epoxides etc. The reactions are usually carried out through the Si—H bond of the branched siloxanes using a method called hydrosilylation.

In the following section, the present invention is described in much more detail. However, the present invention is not limited to the following example. Hexamethylcyclotrisiloxane and dimethylchlorosilane were purchased from Gelest Inc., USA. Activated carbon and Pt (dvs), Platinum(0)-1,3-divinyl-1,1,3,3-tetramethyldisiloxane complex solution in xylene, Pt 2% were purchased from Aldrich, USA. 3H, 5H-Octamethyltetrasiloxane was purchased from Alfa Aesar, USA. Pd/C, Palladium on activated carbon (5% Pd) was purchased from Acros organic, USA. Allyl methacrylate was purchased from TCI, Japan.

DESCRIPTION OF PREFERRED EMBODIMENTS

Figure 5:
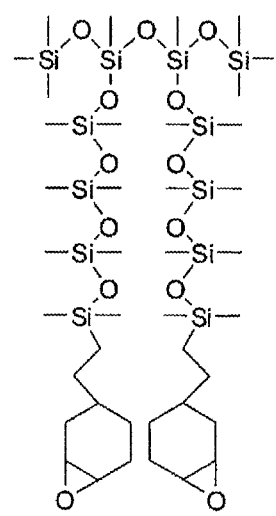
FIG. 5 shows the structure of a novel UV curable branched siloxane (epoxy-Si-12).

In preferred embodiments, the invention is a synthesis for a novel UV curable branched siloxane (epoxy-Si-12) illustrated in FIG. 5. From the previously synthesized Si-14 the siloxane chains were shortened because of the new synthetic route. Epoxide groups were selected to be used for crosslinking. Functionalized Si-12 with epoxides showed a lower UV shrinkage than methacrylate based crosslinking. The synthesis was carried out using conventional organic synthetic techniques. The characterization of the materials were conducted by NMR (VARIAN 400 MHz), GC/MS (Agilent Technologies 6890N attached with HP-5MS capillary column, Agilent), CI-MASS (Dionex ultimate 3000) and MALDI-MASS (VARIAN Pro MALIDI 12 Tesla).

Figure 6:
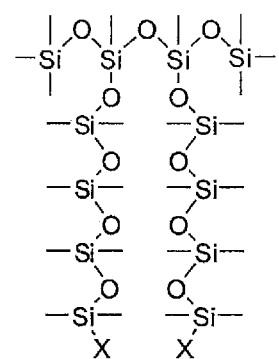
FIG. 6 shows the structure of functionalized UV curable branched siloxanes, in this case a functionalized-Si-12, wherein X represents a chemical moiety, such as a photocurable and or a crosslinkable functional group.

In further preferred embodiments the invention relates to the synthesis of other functionalized novel UV curable branched siloxanes (functionalized-Si-12) illustrated in FIG. 6, where in X represents a photocurable functional group.

The properties of epoxy-Si-12 were investigated; appearance, ratio of silicon content, vapor pressure, viscosity, and shrinkage after the UV cure. The ratio of silicon content was calculated from the molecular weight of the monomer. The vapor pressure was measured by evacuating a chamber containing epoxy-Si-12 submerged in liquid nitrogen. Then by sealing off the vacuum the pressure was measured after the epoxy-Si-12 was thawed. The viscosity was measured by a Physica MCR 500 Rheometer. The UV shrinkage was calculated from the difference of film thickness on substrates by the use of an ellipsometer (J. A. Woollam) before and after the UV cure.

Figure 7:
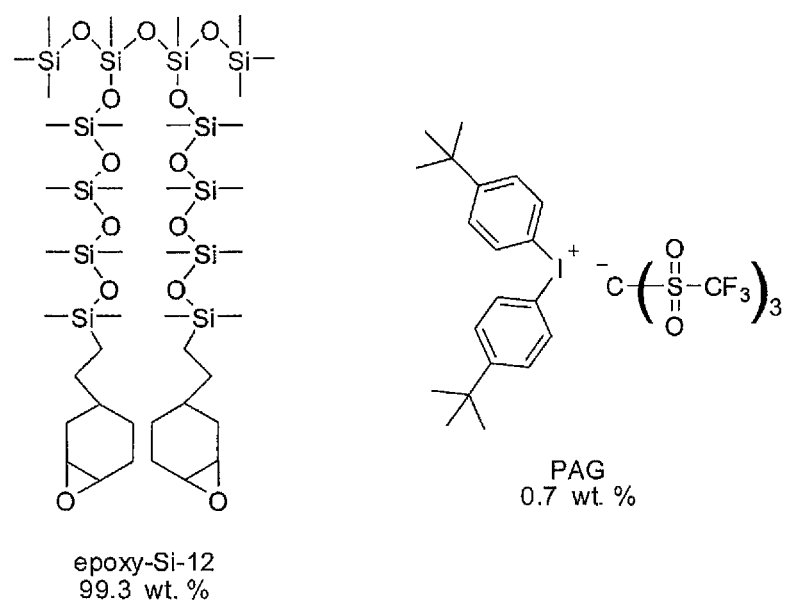
FIG. 7 shows the mixture of epoxy Si-12 and PAG (photo acid generator) used in the formulation to spin coat a planarizing layer.

Initially the spin coat study of epoxy-Si-12 was carried out on bare silicon wafers. Solvents such as PGMEA, PGME, cyclohexanone or butyl alcohol, were not added into the formulation. Only 0.7 wt. % of PAG (photo acid generator), an example of which is illustrated in FIG. 7, was added to the epoxy-Si-12 to initiate crosslinking under the UV exposure. The spin rate of the substrates were set to 2500 rpm. In one embodiment the photoacid generator is bis(4-tert-butylphenyl)iodonium tris(trifluoromethylsulfonyl)methanide. The drop amount of epoxy-Si-12 on 1 inch×1 inch silicon substrates was 200 µl. The film thickness after UV exposure was measured by ellipsometry. All procedures were carried out in a yellow room (UV cut-off filtered room).

Figure 8:
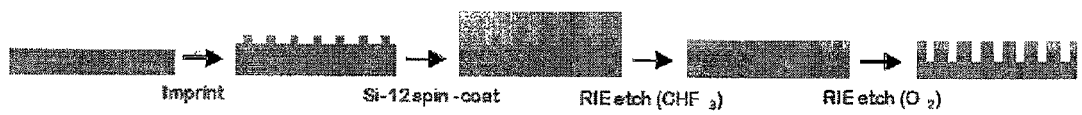
FIG. 8 shows the process flow, the formulation used, and the target stack dimensions.
Figure 8:
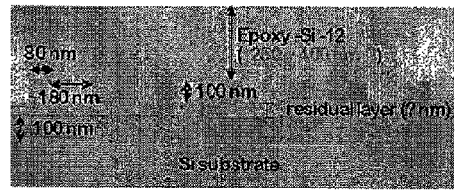

The S-FIL/R demonstration using epoxy-Si-12 was carried out. The process flow, the formulation used, and the target stack dimensions can be seen in FIG. 8. The process consists of several steps; 1) substrate preparation, 2) imprint test features, 3) planarization using epoxy-Si-12, 4) $CHF_3$ etch, 5) $O_2$ etch.

In the first step, the substrates were coated with an underlayer, NCI-NIL-01 (Nissan Chemical Industries, Ltd., Japan). The purposes of such a material are to function as a transfer layer, improve adhesion, and a hard mask for a subsequent etch process to the silicon substrate. In the second step, imprints were carried out on a commercial imprint tool, Imprio 100 (Molecular Imprints Inc., USA) installed at the University of Texas at Austin. A quartz template (mold) with 80 nm lines and 180 nm spaces was also purchased by the University of Texas at Austin. The template was pre-treated with a fluorinated surface treatment (Tridecafluoro-1,1,2,2-tetrahydro octyldimethylchlorosilane from Gelest Inc., USA) as a release layer before imprinting. In the third step, $CHF_3$ etch was carried out on an Oxford Plasmalab 80 to remove excess epoxy-Si-12 layer. The etch ratio of epoxy-Si-12 was determined to reach the correct etch depth. In the last step, $O_2$ etch was carried out to break through the organic layer. SEM (Zeiss Neon 40) was used to measure stack thickness and etch depth after each step except for the first.

The new synthetic route to obtain Si-12 was successfully developed and is illustrated in FIG. 9. The optimized reaction to the final product, Si-12, took only two steps. This is a tremendous improvement in which the desired product can be made in significantly higher yields and with fewer steps compared to previous synthetic routes. The starting materials are relatively cheap and commercially available. The novel synthetic route has also been shown to be easily scalable.

Si-12 has two Si—H bonds, which can be converted to UV curable branched siloxanes. The synthetic path to epoxy-Si-12 is shown in FIG. 10. This type of reaction is referred to as a hydrosilylation. The reaction was successfully carried out and product was recovered in high yields (87%).

EXAMPLE 1

Synthesis of Asymmetric Linear Siloxane (b) (m=2, X=Cl)

A 2 L round bottomed glass flask equipped with a 250 ml addition funnel was prepared. Hexamethylcyclotrisiloxane (116.7 g, 0.524 mol), activated carbon (2.151 g) and hexanes (330 ml) were added to the flask. Dimethylchlorosilane (88.5 ml, 0.795 mol) and hexanes (110 ml) were added to the addition funnel. The dimethylchlorosilane solution was slowly added drop-wise over one hour under $N_2$ at room temperature. The solution was stirred vigorously overnight. The reaction was monitored by GC/MS periodically; if unreacted Hexamethylcyclotrisiloxane was still present over 20%, additional activated carbon and dimethylchlorosilane was added. The solution was filtered through 0.2 μm PTFE membrane to remove activated carbon. The solvent was removed under reduced pressure on a rotary-evaporator. Distillation under vacuum (below 10 Torr) at 170° C. was carried out to purify the product. 129.6 g of the desirable compound was obtained as a colorless liquid. CG/MS spectra showed 99.7% purity. The yield of reaction was 77.9%. $^1$H NMR (CDCl$_3$): δ=4.69 (m, 1H), 0.43 (s, 6H), 0.17 (d, J$_2$=2.80 Hz, 6H), 0.11 (s, 6H), 0.06 (s, 6H). $^{13}$C NMR (CDCl$_3$): δ=4.06, 0.88, 0.80, 0.68. $^{29}$Si{$^1$H} NMR (CDCl$_3$): δ=3.75, −6.63, −18.94, −19.27. $^{29}$Si NMR (CDCl$_3$): δ=3.75, −6.63 (J$_{Si-H}$=203.98 Hz), −18.94, −19.27.

EXAMPLE 2

Synthesis of Branched Siloxane (c) (n=2, m=3)

A 500 ml round bottomed glass flask equipped with a 100 ml addition funnel was prepared. Pd/C (0.16 g), water (1.9 g, 0.106 mol) and THF (175 ml) were added to the flask. 3H, 5H-octamethyltetrasiloxane (10.0 g, 0.035 mol) and THF (75 ml) were added to the addition funnel. The solution was added slowly drop-wise into the flask and after complete addition the reaction was stirred at room temperature for 6 hours. The solution was filtered through acid washed Celite™ to remove Pd/C. A 3 L round bottomed glass flask with a 250 ml addition funnel was prepared. The previously synthesized asymmetric linear siloxane (b) (56.4 g, 0.178 mol), triethylamine (27.8 g, 0.275 mol) and diethyl ether (700 ml) were added to the flask under positive N$_2$ pressure. The filtrate from the Celite™ filtration was added into the addition funnel and dropped slowly into the flask at 0° C. As soon as the addition was complete the ice-bath was removed and the suspension was stirred overnight at room temperature. Water (1 L) was added to the solution to quench excess amounts of asymmetric linear siloxane before the aqueous and organic layers were separated. The organic portion was washed three times with water and dried over magnesium sulfate. The magnesium sulfate was removed by gravity filtration before the solution was reduced in vacuo. Distillation using a Kugelrohr apparatus at 170° C. and at 2 Torr was carried out to remove byproducts as well as impurities. 28.9 g of a colorless liquid was obtained (93.1% yield). $^1$H NMR (CDCl$_3$): δ=4.68 (m, 2H), 0.17 (d, J=2.80 Hz, 12H) 0.08 (d, J=0.40 Hz, 18H), 0.07 (d, J=1.20 Hz, 12H), 0.06 (s, 12H), 0.05 (s, 12H), 0.03 (s, 6H). $^{13}$C NMR (CDCl$_3$): δ=1.67, 1.04, 0.96, 0.85, 0.69, −2.27. $^{29}$Si{$^1$H} NMR (CDCl$_3$): δ=7.70, −7.00, 19.95, −21.82, −22.08, −66.98. $^{29}$Si NMR (CDCl$_3$): δ=7.70, −7.00 (J$_{SiH}$=203.68 Hz), −19.94, −21.82, −22.08, −66.98. MALDI-MASS: m/z=897.235 (C$_{24}$H$_{74}$O$_{11}$Si$_{12}$Na$^{+1}$).

EXAMPLE 3

Synthesis of Functionalized Branched Siloxane (d) (m=3, n=2, X=methacrylate)

500 ml round bottle glass flask was prepared. The branched siloxane (c) (n=2, m=2) (12.0 g, 13.7 mmol), allyl methacrylate (4.41 g, 34.9 mmol)) and toluene (130 ml) were added in the flask under N$_2$ atmosphere. 25 drops of Pt(dvs) catalyst was added to the solution with vigorous stirring. The solution turned to a yellow color and stirring was continued overnight. The solvent was removed in vacuo. The excess allyl methacrylate was removed under vacuum (1 Torr) at room temperature. 14.9 g of a slightly yellow liquid was obtained in 95.8% yield.

EXAMPLE 4

The new synthetic route to obtain Si-12 was successfully developed and is illustrated in FIG. 9. The optimized reaction to the final product, Si-12, took only two steps. This is a tremendous improvement in which the sought after product can be made in significantly higher yields and fewer steps compared to the previous synthetic route. The starting materials are relatively cheap and commercially available. The novel synthetic route has also been shown to be easily scalable and suitable for industry.

Si-12 has two Si—H bonds, which can be converted to UV curable branched siloxanes. The synthetic path to epoxy-Si-12 is shown in FIG. 10. This type of reaction is referred to as a hydrosilylation. The reaction was successfully carried out using the procedure described in Example 3 and the product was recovered in high yields (87%).

EXAMPLE 5

Properties of Epoxy-Si-12

The appearance of epoxy-Si-12 was a slightly yellowish liquid. It is speculated that the reason for the color of the product is due to small amounts of catalyst that were not removed completely in the purification process. The material has a silicon content of 30.0%, which is sufficiently high to withstand an O$_2$ etch process. The vapor pressure is 0.65 Torr at 25° C. The viscosity is 29 cP at 25° C. Both of the properties meet the requirements of an excellent planarizing material. The UV shrinkage was only 2.2%, which was lower than methacrylate derivatives (Si-14 was 5.1%). The all properties are summarized in FIG. 11.

EXAMPLE 6

Spin-Coat Study of Epoxy-Si-12

Figure 12:
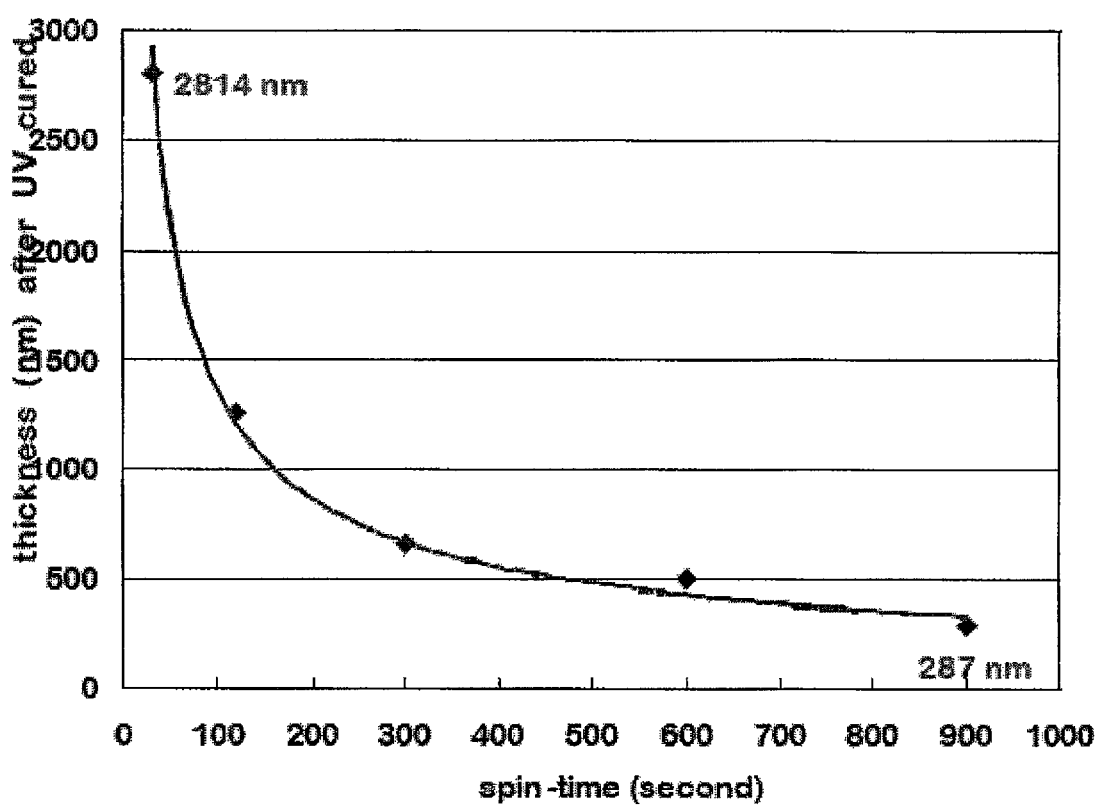
FIG. 12 shows the obtained spin-curve for the spin-coat study of epoxy-Si-12.

The obtained spin-curve is shown in FIG. 12. The result indicated that approximately 150 seconds of spin time is necessary to give a film thickness in less than 1.0 μm. The data was useful for subsequent S-FIL/R demonstration.

EXAMPLE 7

S-FIL/R Demonstration Using Epoxy-Si-12 Resist [6]

Step 1. NCI-NIL-01 (Nissan Chemical) was spin-coated to approximately 100 nm thickness on bare silicon substrates as an underlayer.

Figure 13:
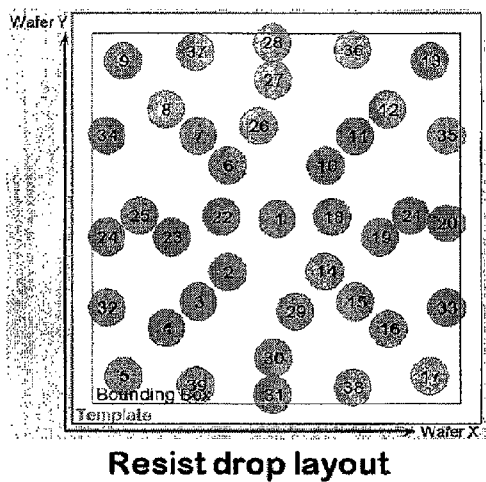
FIG. 13 shows the optimized imprint dispense pattern.

Step 2. Imprints with an 80 nm lines and spaces template on an Imprio 100® were carried out. One of the features of SFIL is an inkjet dispense system to dispense the liquid resist onto substrates. The optimized imprint dispense pattern is illustrated in FIG. 13. The system was developed to take advantage of an authentic spin coat dispense system in terms of not only residual layer uniformity but also to lower the consumption of resist material. The optimized resist drop layout through the inkjet nozzle resulted in consistent and successful imprint pattern.

Figure 14:
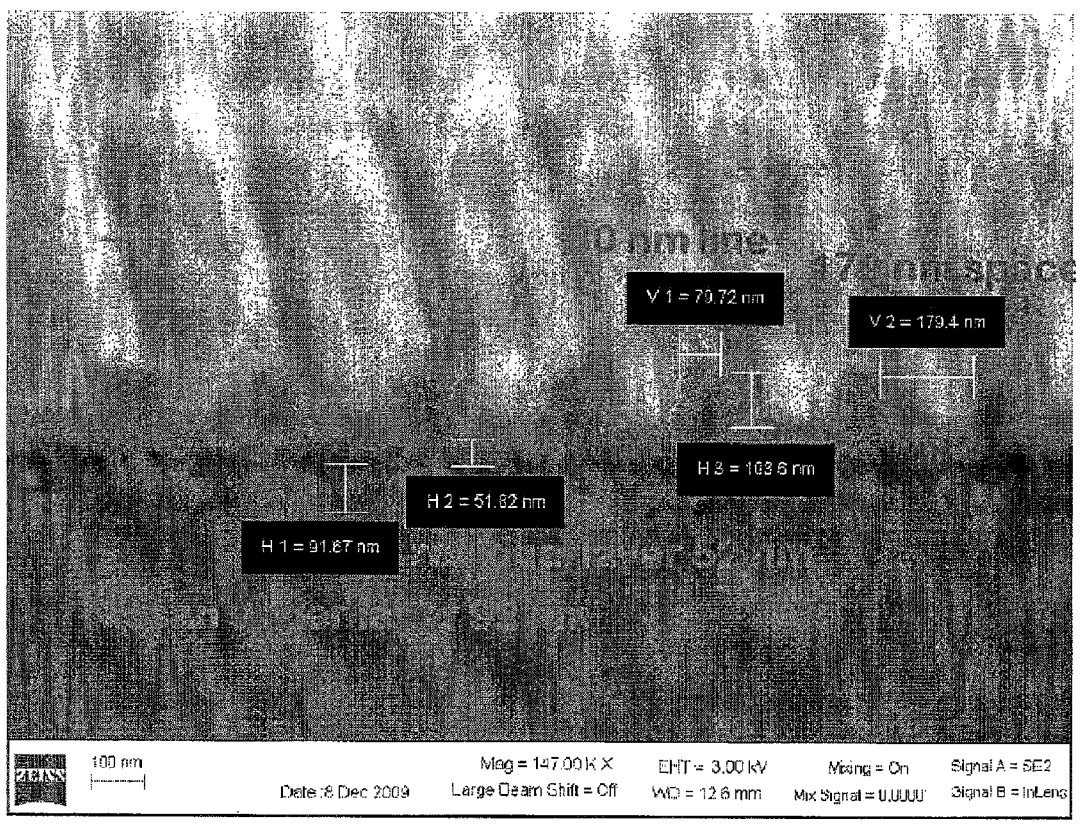
FIG. 14 shows an SEM image of an imprint.

An SEM image of an imprint is shown in FIG. 14. The residual layer was measured to approximately 52 nm, which is a little thicker than for the traditional S-FIL process (less than 20 nm). Further optimization such as lowering the resist volume or changing the imprint force, could reduce the residual thickness. But in the case of the S-FIL/R process, it was acceptable because of the planarizing layer will coat and cover the topography. The imprinted lines and spaces indicated values that corresponds to the features on the template.

Figure 15:
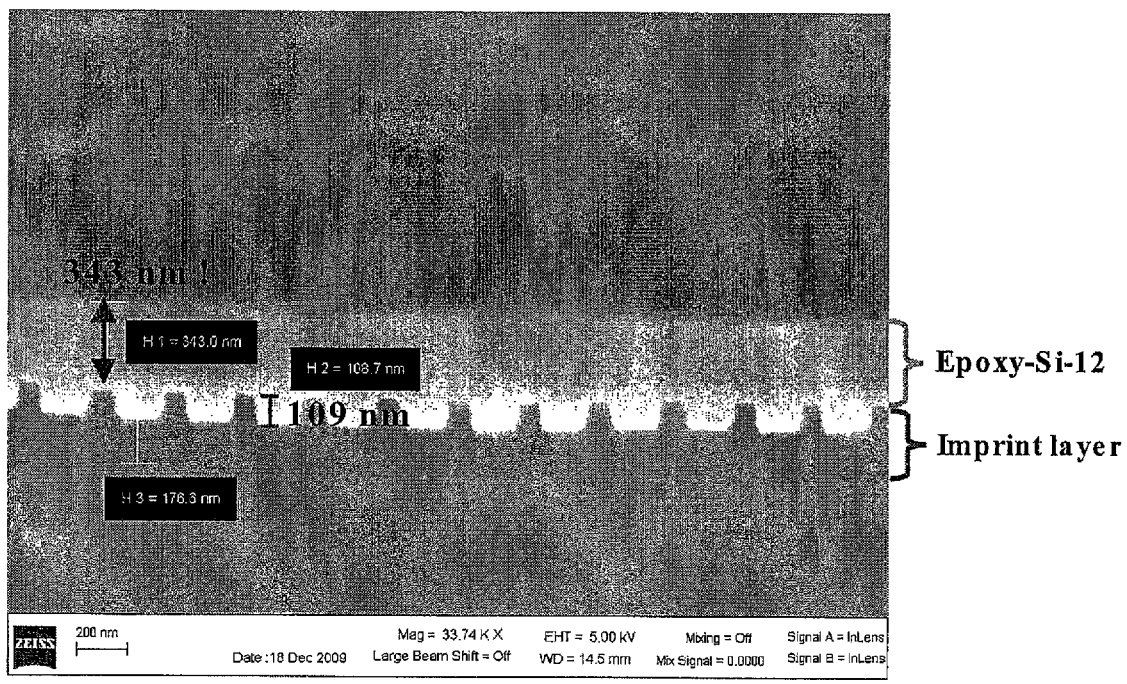
FIG. 15 shows an SEM image after planarization using epoxy-Si-12 was carried out.

Step 3. Planarization using epoxy-Si-12 was carried out and an SEM image is shown in FIG. 15.

Figure 16:
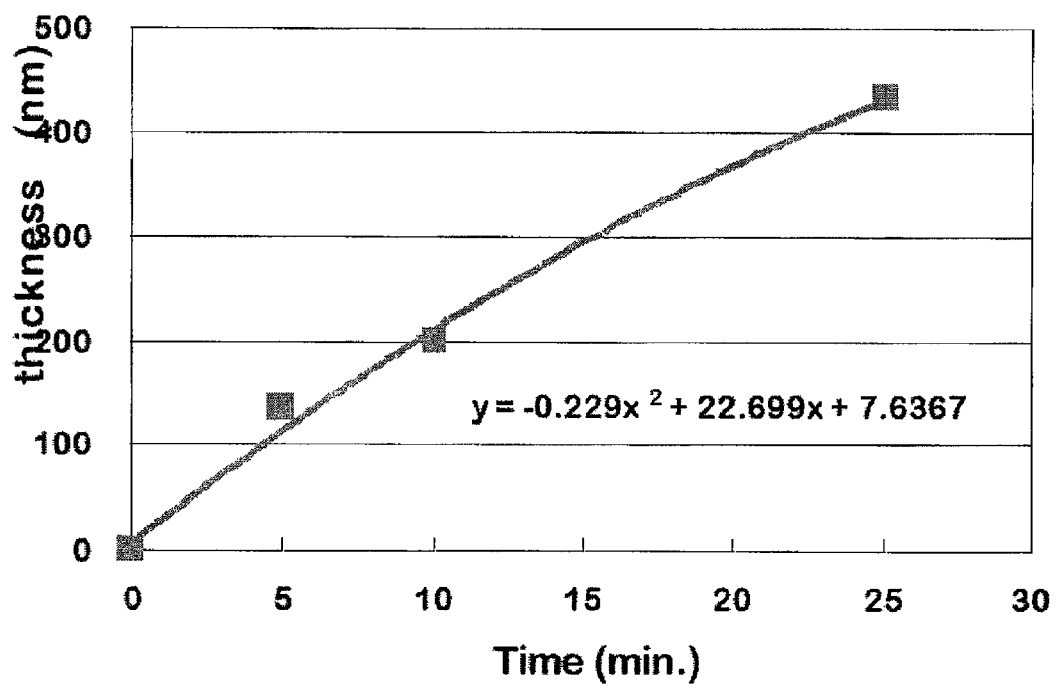
FIG. 16 shows the determined etch rate of epoxy-Si-12.

Step 4. The etch rate of epoxy-Si-12 was determined ($CHF_3$: 20 sccm, $O_2$: 12 sccm, RF: 50 W, DC bias: 192 V, Pressure: 30 mTorr) and is shown in FIG. 16. The actual etching of the planarizing layer was then carried out.

Figure 17:
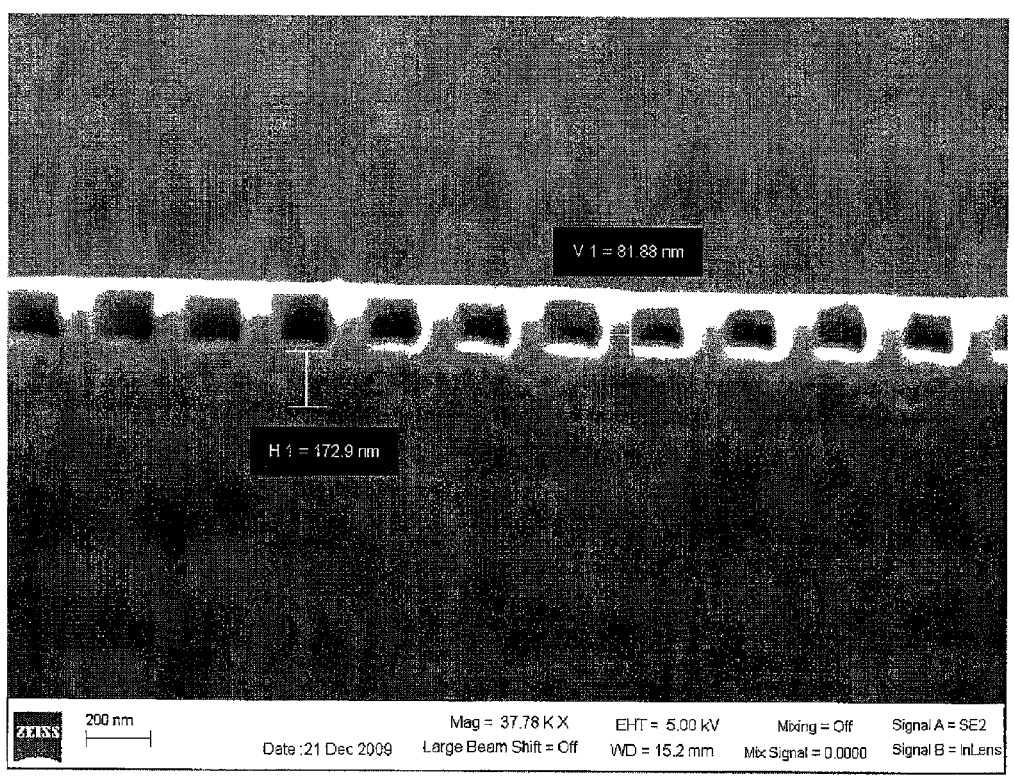
FIG. 17 shows the SEM image after the fluorine etch step.

FIG. 17 shows the SEM image after the fluorine etch step. Epoxy-Si-12 was etched all the way to the top of the imprinted layer after. A total of 10 minutes was required to reach such depth.

Figure 18:
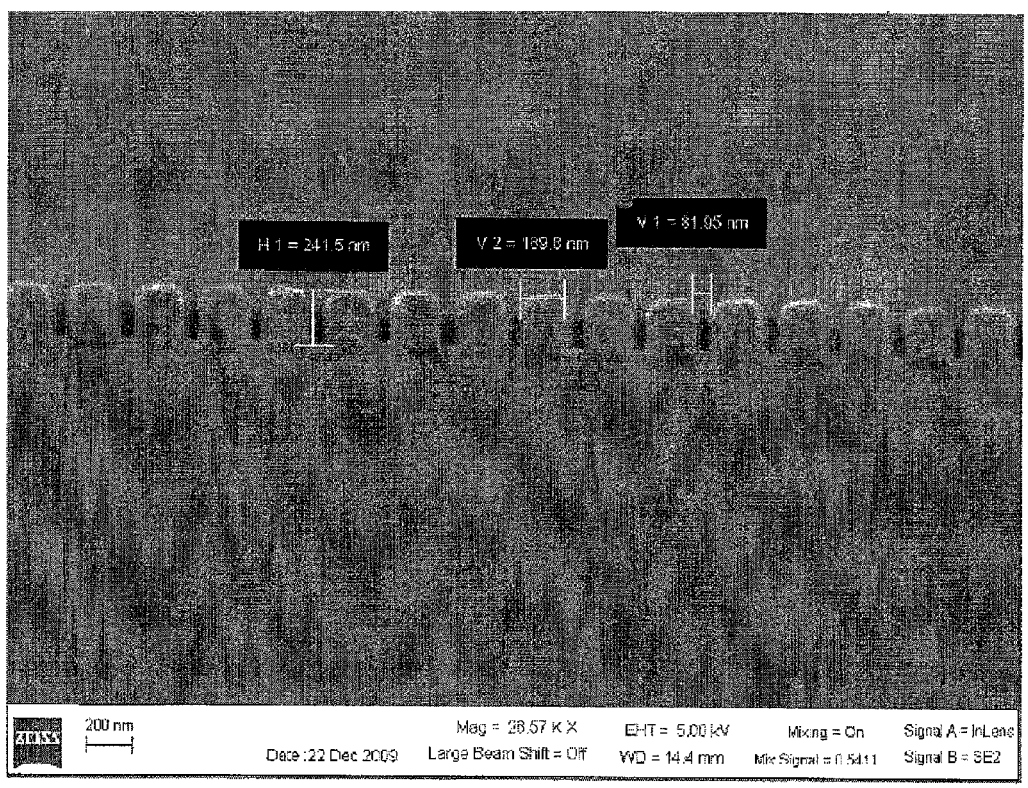
FIG. 18 shows the desired pattern, indicating removal of the organic resist after $O_2$ etching ($O_2$: 3 sccm, Ar: 30 sccm, RF: 90 W, DC bias: 300 V, pressure: 6 mTorr, Etching time: 8 minutes).

Step 5. $O_2$ etching was carried out to break through the organic layer ($O_2$: 3 sccm, Ar: 30 sccm, RF: 90 W, DC bias: 300 V, pressure: 6 mTorr, Etching time: 8 minutes). The result indicated that the organic resist was removed and the desirable pattern was obtained as shown in FIG. 18. The width of lines and spaces was reversed compared to the initial imprint pattern, which indicates that reverse-tone S-FIL was achieved.

REFERENCES

1. Wei-Lun Jen, Frank Palmieri, Brook Chao, Michael Lin, Jianjun Hao, Jordan Owens, Ken Sotoodeh, Robin Cheung, C. Grant Willson, Proceeding of SPIE, 6517, (2007) 65170K
2. Jianjun Hao, Michael W. Lin, Frank Palmieri, Yukio Nishimura, Huang-Lin Chao, Michael D. Stewart, Austin Collins, Kane Jen, C. Grant Wilson, Proceeding of SPIE, 6517, (2007) 651729
3. Koji Yoshino, Akira Kawamata, Hiroaki Uchida, Yoshio Kabe, Chemistry letters, pp. 2133, (1990)
4. Chunxin Zhang, Richard M. Laine, J. Am. Chem. Soc. (2000) 122, 6979-6988)
5. Ryuzaki, Daisuke and Fukuda, Hiroshi. Organic Siloxane Film, Semiconductor Device Using the Same, Flat Panel Display Device, and Raw Material Liquid. U.S. patent application Ser. No. 11/571,017 (published Dec. 18, 2008).
6. S. V. Sreenivasan, D. Resnick, and C. G. Willson. "Using reverse-tone bilayer etch in ultraviolet nanoimprint lithography" Micromagazine, May, 2001.

The invention claimed is:

1. A method, comprising a) providing a substrate and a functionalized branched siloxane Epoxy-Si-12 having the structure shown in FIG. 5; b) spin-coating said functionalized branched siloxane Epoxy-Si-12 on to said substrate; c) curing said spin-coated Epoxy-Si-12; and d) etching said cured functionalized branched siloxane Epoxy-Si-12 on said substrate.

2. The method of claim 1, wherein the functionalized branched siloxane Epoxy-Si-12 is UV cured in step c).

3. The method of claim 1, wherein the functionalized branched siloxane Epoxy-Si-12 is in a mixture with a photo acid generator.

* * * * *